United States Patent
Sesselmann (10) Patent No.: US 10,624,401 B1
(45) Date of Patent: *Apr. 21, 2020

(54) SYSTEMS FOR CONTROLLING ODOR (71) Applicant: ScentLok Technologies, Inc., Muskegon, MI (US)

(72) Inventor: Gregory J. Sesselmann, Muskegon, MI (US)

(73) Assignee: ScentLok Technologies, Inc., Muskegon, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/046,421

(22) Filed: Jul. 26, 2018

Related U.S. Application Data (63) Continuation of application No. 15/381,665, filed on Dec. 16, 2016, now Pat. No. 10,034,506, which is a
(Continued)

(51) Int. Cl.
*A61L 9/014* (2006.01)
*A41D 31/02* (2019.01)
(Continued)

(52) U.S. Cl.
CPC ................ *A41D 31/02* (2013.01); *A41B 1/08* (2013.01); *A41B 17/00* (2013.01); *A41D 1/02* (2013.01);
(Continued)

(58) Field of Classification Search
CPC ........ A41D 1/02; A41D 1/08; A41D 2400/36; A41D 2500/00; A41D 2600/108;
(Continued)

(56) References Cited

U.S. PATENT DOCUMENTS 2,959,789 A 11/1960 Mills et al.
3,130,416 A 4/1964 Mitchell et al.
(Continued)

FOREIGN PATENT DOCUMENTS

DE 29 51 827 A1 7/1981
DE 33 04 349 A1 8/1984
(Continued)

OTHER PUBLICATIONS

"Read the Story," printed from website www.myfoxtwincities.com, article created and edited Nov. 9, 2006, 2 pages.
(Continued)

*Primary Examiner* — Arti Singh-Pandey
(74) *Attorney, Agent, or Firm* — Foley & Lardner LLP (57) ABSTRACT

A jacket has a torso portion, a pair of underarm portions adjacent the torso portion, and a pair of arms, one of each of the arms being adjacent one of each of the underarm portions, at least one of the torso portion and the pair of arms defining a first area and the pair of underarm portions defining a second area. The article further includes a first assembly including one or more scent control materials provided within the first area defined by a cloth and a second assembly including one or more scent control materials provided within the second area defined by the cloth, the second assembly having a different composition than the first assembly. The first assembly and the second assembly together include activated carbon and at least one of carbon treated to adsorb hydrogen sulfide, zeolite, ammonia stone, and carbon treated to adsorb mercaptan.

20 Claims, 5 Drawing Sheets

Related U.S. Application Data continuation of application No. 14/203,286, filed on Mar. 10, 2014, now Pat. No. 9,522,207, which is a continuation of application No. 13/691,052, filed on Nov. 30, 2012, now abandoned, application No. 15/440,813, filed on Feb. 23, 2017, now Pat. No. 10,034,505, which is a continuation of application No. 14/334,399, filed on Jul. 17, 2014, now Pat. No. 9,579,626, which is a continuation-in-part of application No. 14/203,286, filed on Mar. 10, 2014, now Pat. No. 9,522,207, which is a continuation of application No. 13/691,052, filed on Nov. 30, 2012, now abandoned.

(60) Provisional application No. 61/565,665, filed on Dec. 1, 2011.

(51) Int. Cl.
  *A41D 1/02* (2006.01)
  *A41D 31/00* (2019.01)
  *A41D 1/08* (2018.01)
  *A41D 3/00* (2006.01)
  *A41D 13/00* (2006.01)
  *A41B 1/08* (2006.01)
  *A41B 17/00* (2006.01)
  *A41D 31/28* (2019.01)

(52) U.S. Cl.
  CPC .......... *A41D 1/08* (2013.01); *A41D 3/00* (2013.01); *A41D 13/0015* (2013.01); *A41D 31/00* (2013.01); *A41D 31/285* (2019.02); *A61L 9/014* (2013.01); *A41B 2400/22* (2013.01); *A41B 2400/36* (2013.01); *A41D 2400/10* (2013.01); *A41D 2400/22* (2013.01); *A41D 2400/36* (2013.01); *A41D 2500/00* (2013.01); *A41D 2600/108* (2013.01)

(58) Field of Classification Search
  CPC ...... A41D 31/00; A41D 31/005; A41D 31/02; A61L 9/014; A61Q 15/00; B01J 20/041; B01J 20/043; B01J 20/103; B01J 20/165; B01J 20/20
  See application file for complete search history.

(56) References Cited

U.S. PATENT DOCUMENTS

| | | |
|---|---|---|
| 3,200,427 A | 8/1965 | Daley |
| 3,333,585 A | 8/1967 | Barghine et al. |
| 3,586,596 A | 6/1971 | Ainsworth et al. |
| 3,744,534 A | 7/1973 | Henry et al. |
| 3,783,085 A | 1/1974 | Pearson et al. |
| 3,837,006 A | 9/1974 | Laseman |
| 3,850,785 A | 11/1974 | McQuade et al. |
| 3,852,897 A | 12/1974 | Bridge et al. |
| 3,903,259 A | 9/1975 | Hart |
| 3,920,020 A | 11/1975 | Kraskin |
| 3,922,723 A | 12/1975 | Popper |
| 3,959,556 A | 5/1976 | Morrison |
| 4,045,609 A | 8/1977 | Hart |
| 4,046,939 A | 9/1977 | Hart |
| 4,067,210 A | 1/1978 | Arons et al. |
| 4,099,342 A | 7/1978 | Singh |
| 4,117,552 A | 10/1978 | Simpson |
| 4,182,335 A | 1/1980 | Matrullo |
| 4,186,499 A | 2/1980 | Massok et al. |
| 4,186,502 A | 2/1980 | Foster |
| 4,217,386 A | 8/1980 | Arons et al. |
| 4,228,549 A | 10/1980 | Rispoli |
| 4,244,059 A | 1/1981 | Pflaumer |
| 4,285,068 A | 8/1981 | Ross |
| 4,302,899 A | 12/1981 | Dehart |
| 4,343,853 A | 8/1982 | Morrison |
| 4,433,024 A | 2/1984 | Eian |
| 4,454,191 A | 6/1984 | Von Blucher et al. |
| 4,455,187 A | 6/1984 | Von Blucher et al. |
| 4,460,708 A | 7/1984 | Stuetz |
| 4,504,290 A | 3/1985 | Pontius |
| 4,510,193 A | 4/1985 | Blucher et al. |
| 4,515,761 A | 5/1985 | Plotzker |
| 4,525,410 A | 6/1985 | Hagiwara et al. |
| 4,539,982 A | 9/1985 | Bailly |
| 4,565,727 A | 1/1986 | Giglia et al. |
| 4,609,245 A | 9/1986 | Sakschek |
| 4,617,230 A | 10/1986 | Shah et al. |
| 4,663,780 A | 5/1987 | Rawlings et al. |
| 4,677,019 A | 6/1987 | Von Blucher |
| 4,715,857 A | 12/1987 | Juhasz et al. |
| 4,718,122 A | 1/1988 | Steverson |
| 4,722,477 A | 2/1988 | Floyd |
| 4,790,040 A | 12/1988 | Grilliot et al. |
| 4,797,318 A | 1/1989 | Brooker et al. |
| 4,810,102 A | 3/1989 | Norton |
| 4,817,594 A | 4/1989 | Juhasz |
| 4,856,111 A | 8/1989 | Sholes |
| 4,860,382 A | 8/1989 | Markwell |
| 4,868,019 A | 9/1989 | Knickerbocker |
| 4,872,220 A | 10/1989 | Haruvy et al. |
| 4,874,129 A | 10/1989 | Disapio et al. |
| 4,883,021 A | 11/1989 | Ducharme et al. |
| 4,901,370 A | 2/1990 | Suda |
| 4,917,301 A | 4/1990 | Munteanu |
| H823 H | 10/1990 | Conkle et al. |
| 4,982,467 A | 1/1991 | Mizusawa et al. |
| 5,002,183 A | 3/1991 | Okano |
| 5,009,308 A | 4/1991 | Cullen et al. |
| 5,017,424 A | 5/1991 | Farnworth et al. |
| 5,022,553 A | 6/1991 | Pontius |
| 5,024,008 A | 6/1991 | Maples |
| 5,025,507 A | 6/1991 | Kirby |
| 5,042,088 A | 8/1991 | Sherrod et al. |
| 5,085,914 A | 2/1992 | Perdelwitz et al. |
| 5,088,116 A | 2/1992 | Gould |
| 5,092,008 A | 3/1992 | Okubo |
| 5,103,500 A | 4/1992 | Nager et al. |
| 5,112,666 A | 5/1992 | Langston |
| 5,117,821 A | 6/1992 | White |
| 5,129,735 A | 7/1992 | Neal et al. |
| 5,154,960 A | 10/1992 | Mucci et al. |
| 5,159,718 A | 11/1992 | Moyer |
| 5,161,686 A | 11/1992 | Weber et al. |
| 5,165,964 A | 11/1992 | Imai |
| 5,183,656 A | 2/1993 | Uesaka et al. |
| 5,383,236 A | 1/1995 | Sesselmann |
| 5,445,863 A | 8/1995 | Slagle et al. |
| 5,539,930 A | 7/1996 | Sesselmann |
| 5,585,107 A | 12/1996 | Vickers |
| 5,678,247 A | 10/1997 | Vickers |
| 5,790,987 A | 8/1998 | Sesselmann |
| 6,000,057 A | 12/1999 | Newman |
| 6,009,559 A | 1/2000 | Sesselmann |
| 6,134,718 A | 10/2000 | Sesselmann |
| 7,939,015 B1 | 5/2011 | Elrod |
| 8,066,939 B2 | 11/2011 | Elrod |
| 8,069,496 B2 | 12/2011 | Sesselmann |
| 8,187,533 B2 | 5/2012 | Elrod |
| 8,257,648 B2 | 9/2012 | Elrod |
| 8,329,096 B2 | 12/2012 | Elrod et al. |
| 8,404,180 B1 | 3/2013 | Elrod |
| 8,557,177 B1 | 10/2013 | Elrod |
| 9,522,207 B1 * | 12/2016 | Sesselmann ............ A61L 9/014 |
| 9,579,626 B1 * | 2/2017 | Sesselmann ............ B01J 20/20 |
| 10,034,505 B1 * | 7/2018 | Sesselmann ............ B01J 20/20 |
| 10,034,506 B1 * | 7/2018 | Sesselmann ............ A61L 9/014 |
| 2008/0147028 A1 | 6/2008 | Luna et al. |

FOREIGN PATENT DOCUMENTS

| | | |
|---|---|---|
| DE | 39 24 034 A1 | 1/1991 |
| DE | 40 03 765 A1 | 8/1991 |

(56) References Cited

FOREIGN PATENT DOCUMENTS

| | | |
|---|---|---|
| EP | 0 099 758 | 2/1984 |
| EP | 0 118 618 B1 | 11/1986 |
| EP | 0 144 553 B1 | 11/1987 |
| EP | 0 260 841 A1 | 3/1988 |
| EP | 0 053 936 | 4/1989 |
| GB | 1 173 143 | 10/1969 |
| GB | 1 301 101 | 12/1972 |
| GB | 2 067 095 A | 7/1981 |
| GB | 2 127 389 | 4/1984 |
| GB | 2 207 390 A | 2/1989 |
| WO | WO-97/46878 | 12/1997 |

OTHER PUBLICATIONS

"British Breakthrough—Garfil Nonwovens," Nonwovens Industry, Apr. 1984, pp. 10-14, vol. 15, No. 4, Rodman Publications, Inc., Ramsey, NJ.
"Charcoal Cloth Comes of Age for Body Protection," The ASA Newsletter, Apr. 3, 1992, pg. 13, Issue No. 29 (Ed. Colonel Richard Price).
"Hunter's Edge Markets Scent-Absorbing Suit," Sunday Montgomery Advertiser, Dec. 6, 1992, Business Section, Montgomery, Alabama.
"Outdoor Life Deer Hunter's Yearbook," 1989, p. 28, Popular Science Books, New York (3 pgs. total).
306 Adsorption Control Devices Theory and Design, printed on Dec. 19, 2012, retrieved from URL:www.arb.ca.gov/capmanuals/cntrldev/vocs/306adsorbers.htm, 7 pages.
A.L.S. Enterprises, Inc., Decision on Appeal, United States Patent and Trademark Office, Board of Patent Appeals, Appeal 2009-014648, Mar. 29, 2010, 59 pages.
Advertisement for Scent Control Powder, Buckmasters's Whitetail Magazine, Nov. 1991, pg. 75 (1 page).
Alexandroff et al., "PBI Saratoga: New and Improved CWU/66P Chemical Protective Clothing System for Aircrew Application" (undated).
Arons et al., "Activated Carbon Fiber and Fabric Achieved by Pyrolysis and Activation of Phenolic Precursors," Textile Research Journal, Jan. 1972, pp. 60-63, vol. 42, No. 1, Textile Research Institute, Princeton, New Jersey.
Arons et al., "Sorption Characteristics of Activated Carbon Fabric," Textile Research Journal, Sep. 1973, pp. 539-543, vol. 43, No. 9, Textile Research Institute, Princeton, New Jersey.
Arons et al., "Sorptive Textile Systems Containing Activated Carbon Fibers," Textile Research Journal, Nov. 1974, pp. 874-883, vol. 44, No. 11, Textile Research Institute, Princeton, New Jersey.
Blücher, "Status of Today—May 1991" (undated).
Bluecher, "SaratogaTM by Bluecher: Saratogo—Philosophy" (undated).
Chemical Warfare Defense Handbook, Nov. 1989.
Clinton, Brad, 37 C.F.R. Sec. 1,132 Declaration, Oct. 29, 1995, 3 pages.
Daul, George C. et al., "Studies on the Partial Carboxymethylation of Cotton," Textile Research Journal, Dec. 1952, pp. 787-792 with cover and table of contents pages, vol. XXII, No. 12, Textile Research Institute, New York, NY.
David Hughes, "USAF May Speed Production of New Suits to Protect Crews from Chemical Weapons," Aviation Week & Space Technology, Aug. 20, 1990, pp. 27.
Dawson, Jim; Whitetail Hunting; 1982; cover page, copyright page, pp. 20-22, 86-88, 95-97; Stackpole Books, Harrisburg, PA.
Declaration of Gregory J. Sesselmann, dated Apr. 3, 2003.
Derek Griffiths, "The Mark IV: State-of-the-Art in British NBC Protection," Nuclear, Biological and Chemical Defense and Technology International, 1987, pp. 37-40, vol. 2, No. 1, NBC Defense International Ltd., New York, NY.
Edberg, Keith, Declaration, Mar. 22, 2007, 5 pages.
Edberg, Keith, Supplemental Declaration, Sep. 23, 2008, 28 pages.
E-mail from T.R. Michels, dated, Nov. 27, 2006, 2 pages.
Etling, Kathy, 37 C.F.R. Sec. 1,132 Declaration, Nov. 4, 1993, 3 pages.
Eugene E. Alexandroff, "Saratoga: A New Dimension in CB Protective Clothing," Nuclear, Biological, and Chemical Defense Technology, May 1986, pp. 43-46, vol. 1, No. 2.
Eugene E. Alexandroff, "Saratoga: Carbon Pellet Technology in Chemical Warfare Protective Fabrics," Proc. 2nd Int. Symp. Protection Against Chemical Warfare Agents, Jun. 15-19, 1986, pp. 67-76, Stockholm, Sweden.
Facsimile received from unknown third party dated Aug. 7, 2006 containing statement of an unknown individual, Richard Mellor, regarding odor absorption.
First Office Action in Reexamination of U.S. Pat. No. 5,539,930.
Gary Tate's Chemical Warfare Equipment page, http://www.seanet.com/~gtate/cwappar.htm (printed Nov. 17, 1999).
Geurink, Denny, 37 C.F.R. Sec. 1,132 Declaration, Oct. 21, 1993, 2 pages.
Gilbert et al., "Activated Carbon Fabric Prepared by Pyrolysis and Activation of Phenolic Fabric," Textile Research Journal, Jan. 1975, p. 91, vol. 45, No. 1, Textile Research Institute, Princeton, New Jersey.
Guthrie, John D., "Introduction of Amino Groups into Cotton Fabric by Use of 2-Aminoethylsulfuric Acid," Textile Research Journal, Nov. 1947, pp. 625-629.
Guthrie, John D., "Ion Exchange Cottons," Industrial and Engineering Chemistry, Sep. 1952, pp. 2187-2189.
Hawley's Condensed Chemical Dictionary, 14th Edition, 2002, slected exerpts.
Hill, James C., 37 C.F.R. Sec. 1,132 Declaration, Jan. 12, 1993, 3 pages.
Hill, Jim, Declaration, Mar. 22, 2007, 4 pages.
Hill, Jim, Supplemental Declaration, Sep. 22, 2008, 6 pages.
Hunter's Edge Outfitters, "The Hunter's Edge Story," 2 pgs. (dated at least as early as Mar. 28, 1994).
Jim Dawson, "Whitetail Hunting," 1982, p. 87, Stackpole Books, Harrisburg (3 pgs. total).
Jurgens, Julian F. et al., "Phosphorylated Cotton Cellulose as a Cation-Exchange Material," Textile Research Journal, Jan. 1948, pp. 42-44.
Kim et al., "Development of Improved Permeable and Impermeable Material for Chemical Protective Clothing," 88 pgs., Jun. 1985, Celanese Research Company, Summit, New Jersey.
KOH Impregnated Coal Based Carbon, Prominent Systems Inc.— Coconut Based Activated Carbon, printed on Dec. 19, 2012, retreived from internet URL:www.prominentinc.com/cbac_impregnated_koh.html, 1 page.
Love, John David, 37 C.F.R. Sec. 1,132 Declaration, Jan. 13, 1992, 3 pages.
Military Specification—Cloth, Camouflage Pattern: Woodland, Cotton and Nylon, MIL-C-44031, Sep. 26, 1980.
Military Specification—Cloth, Laminated, Nylon Tricot Knit, Polyurethane Foam Laminate, Chemical Protective and Flame Resistant, MIL-C-43858B (GL), Jan. 16, 1986.
Military Specification—Cloth, Twill, Camouflage Pattern, Cotton and Nylon for Desert Uniform, MIL-C-44034C, Mar. 28, 1986.
Military Specification—Suit, Chemical Protective, MIL-S-43926H, Mar. 25, 1988.
Military Specification—Suit, Chemical Protective, MIL-S-43926J, Aug. 30, 1991.
Miller, Greg, "Bucks and B.O.," Outdoor Life Deer Hunter's Yearbook, 1990, cover and pp. 25-30.
Notice of Litigation Involving Subject Matter for Which a Patent is Being Sought for U.S. Appl. No. 10/050,203, mailed Apr. 28, 2003, 3 pages.
OdorGard, "Disappearing Act," Buck Masters (dated at least as early as Jan. 3, 1992) (Advertisement).
Original Scent Shield, http://www.bowhunting.net/scentshield, Robinson Laboratories, Inc. (print date unknown).
Paquin, Greg, Declaration, Mar. 22, 2007, 158 pages.
Reeves, Wilson A. et al., "Aminization of Cotton," Textile Research Journal, Aug. 1953, pp. 522-527.

(56) References Cited

OTHER PUBLICATIONS

Reeves, Wilson A. et al., "Chemical and Physical Properties of Aminized Cotton," Textile Research Journal, Aug. 1953, pp. 527-532.
Request for Reexamination of U.S. Pat. No. 5,539,930.
Residential Air Purification Systems, IQAir®, 2012, 20 pages.
Silver Impregnated Coconut Shell Activated Carbon, Prominent Systems, Inc.—Coconut Based Activated Carbon, printed on Dec. 19, 2012, retrieved from internet URL:www.prominenticn.com/cbac_impregnated_silver.html, 1 page.
Tarrell, Everett, Declaration, May 22, 2006, 4 pages.
Undated, unsigned letter received by Applicant's counsel on Feb. 17, 2006 containing anonymous statement regarding sales of chemical warfare suits along with the following enclosures (a) ebay search results dated Feb. 6, 2006; (b) copy of a photograph of mailing envelope and chemical warfare suit and (c) a close-up photograph of chemical warfare suit bearing a fabric date of Feb. 1986 and a second date of Sep. 1986.
Winfield Manufacturing Company, "Technical Bulletin SAr-1: Saratoga in CD Protective Clothing," Winfield Saratoga, Oct. 1984.
Winfield Manufacturing Company, "Technical Bulletin SAr-3: Chemicla Protective PBI Saratoga CWU/66P Air Force Flight Coverall," Winfield Saratoga, Jun. 1989.
www.ext.vt.edu, "A Glossary of Water-Related Terms", printed Dec. 15, 2005, 13 pages.
www.robinsonoutdoors.com/osc/scentcontrol.php, "U of Stink", printed Dec. 14, 2006, 6 pages.
www.trmichaels.com/activatedcarbonscience.htm, from the TRMichaels.com.Webring on Activated Carbon suites, printed Dec. 13, 2006, 32 pages.

* cited by examiner

SYSTEMS FOR CONTROLLING ODOR

CROSS-REFERENCE TO RELATED APPLICATIONS

This application is a continuation of U.S. patent application Ser. No. 15/440,813, entitled "Systems for Controlling Odor," filed on Feb. 23, 2017, which is a continuation of U.S. patent application Ser. No. 14/334,399, entitled "Systems and Methods for Controlling Odor," filed on Jul. 17, 2014, now U.S. Pat. No. 9,579,626, which is a continuation-in-part of U.S. patent application Ser. No. 14/203,286, entitled "Systems and Methods for Controlling Odor," filed on Mar. 10, 2014, now U.S. Pat. No. 9,522,207, which is a continuation of U.S. patent application Ser. No. 13/691,052, entitled "Systems and Methods for Controlling Human Odor," filed on Nov. 30, 2012, which claims the benefit under 35 U.S.C. § 119(e) of U.S. Prov. Pat. App. No. 61/565,665, entitled "Systems and Methods for Controlling Human Odor," filed on Dec. 1, 2011; and is a continuation of U.S. patent application Ser. No. 15/381,665, entitled "Systems for Controlling Odor," filed on Dec. 16, 2016, which is a continuation of U.S. patent application Ser. No. 14/203,286, entitled "Systems and Methods for Controlling Odor," filed on Mar. 10, 2014, now U.S. Pat. No. 9,522,207, which is a continuation of U.S. patent application Ser. No. 13/691,052, entitled "Systems and Methods for Controlling Human Odor," filed on Nov. 30, 2012, which claims the benefit under 35 U.S.C. § 119(e) of U.S. Prov. Pat. App. No. 61/565,665, entitled "Systems and Methods for Controlling Human Odor," filed on Dec. 1, 2011, all of which are hereby incorporated by reference in their entireties.

BACKGROUND

The present disclosure generally relates to systems and methods for controlling or limiting the communication of odors. More specifically, the present disclosure relates to systems and methods for controlling human odor in or on articles of plain colored, camouflaged, or otherwise patterned clothing. Such clothing may be used by hunters, field biologists, nature photographers, and others to reduce the likelihood of detection by target species (e.g., deer, bear, etc.) during hunting or photographing in a natural environment, evasion in a wartime setting, or in other applications.

Humans produce, expel, or otherwise provide a spectrum of odors, some of which are detectable by wild game and other animals and signal the presence of humans. Carbon is widely recognized as an odor-controlling material and is used in various industries to eliminate odors, including the animal photography field, the military clothing field, and the hunting and camouflage fields for changing a human's odor profile. For example, activated carbon formed from coconut shells may be integrated in some camouflage clothing.

Some camouflage clothing for hunters may use activated carbon or charcoal to adsorb (e.g., absorb, take in, mask, control) human odors to thwart animals' acute sense of smell and effectively conceal humans from animals. Adsorption of human odors using carbon has been found to reduce the odor profile of hunters. But use of carbon alone may not adsorb the fullest spectrum of human odor detectable by some target species. Instead, various odors may not be controlled and may still indicate the presence of the human (e.g., hunter, photographer, etc.) to the target species.

Applicant is the inventor of the technologies disclosed in U.S. Pat. No. 5,383,236, issued Jan. 24, 1995, which is incorporated by reference herein in its entirety. U.S. Pat. No. 5,383,236 discloses the use of odor-controlling materials, including activated charcoal, chlorophyll, baking soda, activated alumina, soda lime, zeolite, calcium oxide, and potassium permanganate. However, U.S. Pat. No. 5,383,236 teaches the use of only a single odor-controlling material. U.S. Pat. No. 5,383,236 teaches neither the combination of odor-controlling materials nor varying concentrations of a combination of odor-controlling materials in different locations to mask substantially the full spectrum of human odor or particular odors from a specific body area from a target species.

SUMMARY

One embodiment of the present disclosure relates to a scent reducing article of clothing includes material arranged to form a jacket. The article includes a cloth having one or more pieces of the material arranged to form the jacket, the jacket having a torso portion, a pair of underarm portions adjacent the torso portion, and a pair of arms, one of each of the arms being adjacent one of each of the underarm portions, at least one of the torso portion and the pair of arms defining a first area and the pair of underarm portions defining a second area. The article further includes a first assembly including one or more scent control materials provided within the first area defined by the cloth and a second assembly including one or more scent control materials provided within the second area defined by the cloth, the second assembly having a different composition than the first assembly. The first assembly and the second assembly together include activated carbon and at least one of carbon treated to adsorb hydrogen sulfide, zeolite, ammonia stone, and carbon treated to adsorb mercaptan.

Another embodiment of the present disclosure relates to a scent reducing article of clothing including material arranged to form a shirt. The article includes a cloth having one or more pieces of the material arranged to form the shirt, the shirt having a torso portion, a pair of underarm portions adjacent the torso portion, and a pair of arms, one of each of the arms being adjacent one of each of the underarm portions, at least one of the torso portion and the pair of arms defining a first area and the pair of underarm portions defining a second area. The article further includes a first assembly including one or more scent control materials provided within the first area defined by the cloth and a second assembly including one or more scent control materials provided within the second area defined by the cloth, the second assembly having a different composition than the first assembly. The first assembly and the second assembly together include activated carbon and at least one of carbon treated to adsorb hydrogen sulfide, zeolite, ammonia stone, and carbon treated to adsorb mercaptan.

Yet another embodiment of the present disclosure relates to a scent reducing article of clothing including material arranged to form pants. The article includes a cloth comprising one or more pieces of the material arranged to form the pants, the pants having a pair of leg sections adjacent a groin region, the pair of leg sections defining a first area and the groin region defining a second area. The article further includes a first assembly including one or more scent control materials provided within the first area defined by the cloth and a second assembly including one or more scent control materials provided within the second area defined by the cloth, the second assembly having a different composition than the first assembly. The first assembly and the second assembly together include activated carbon and at least one of carbon treated to adsorb hydrogen sulfide, zeolite, ammonia stone, and carbon treated to adsorb mercaptan.

Still another embodiment of the present disclosure relates to a scent reducing article of clothing including material arranged to form a hunting face mask. The article includes a cloth comprising one or more pieces of the material arranged to form the hunting face mask, the hunting face mask having a head cover and a mouth cover, the head cover configured to envelope at least a portion of a hunter's head and the mouth cover positioned to be at least selectively worn adjacent the hunter's mouth, the head cover defining a first area and the mouth cover defining a second area. The article further includes a first assembly including one or more scent control materials provided within the first area defined by the cloth and a second assembly including one or more scent control materials provided within the second area defined by the cloth, the second assembly having a different composition than the first assembly. The first assembly and the second assembly together include activated carbon and at least one of carbon treated to adsorb hydrogen sulfide, zeolite, ammonia stone, and carbon treated to adsorb mercaptan.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, in which.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
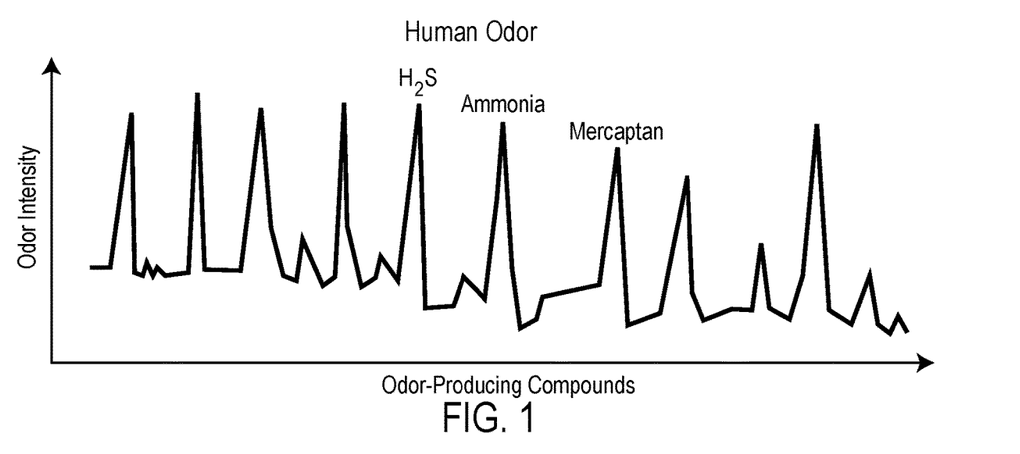
FIG. 1 is a hypothetical odor spectrum for a human with odor intensity on the vertical axis and odor source on the horizontal axis.
Figure 2A:
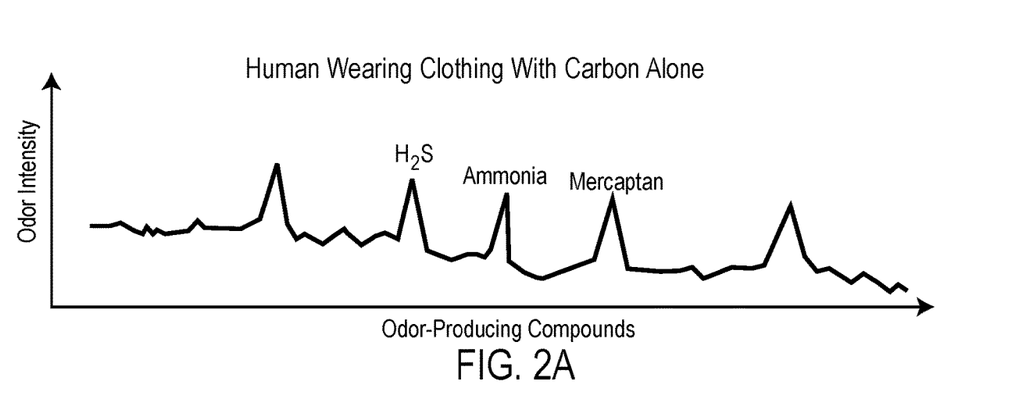
FIG. 2a is a hypothetical odor spectrum for a human wearing clothing including activated carbon alone, according to an exemplary embodiment.
Figure 2B:
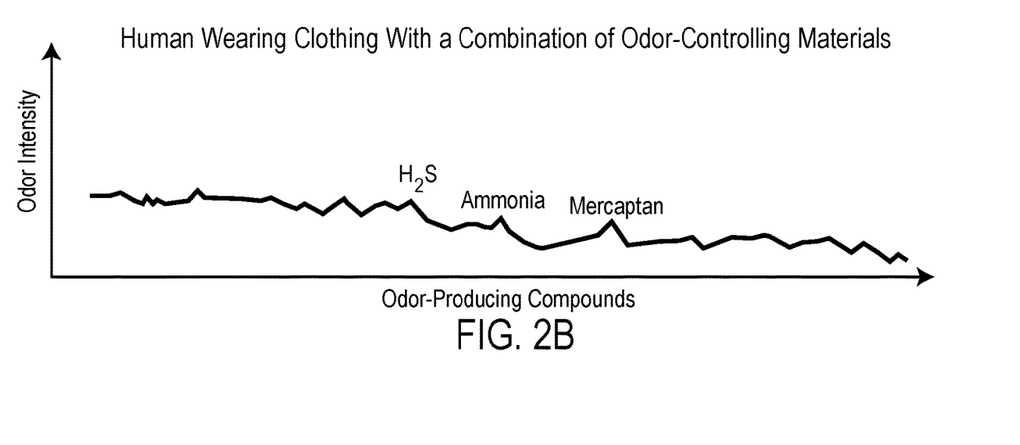
FIG. 2b is a hypothetical odor spectrum for a human wearing clothing including activated carbon combined with additional materials, according to an exemplary embodiment.
Figure 2C:
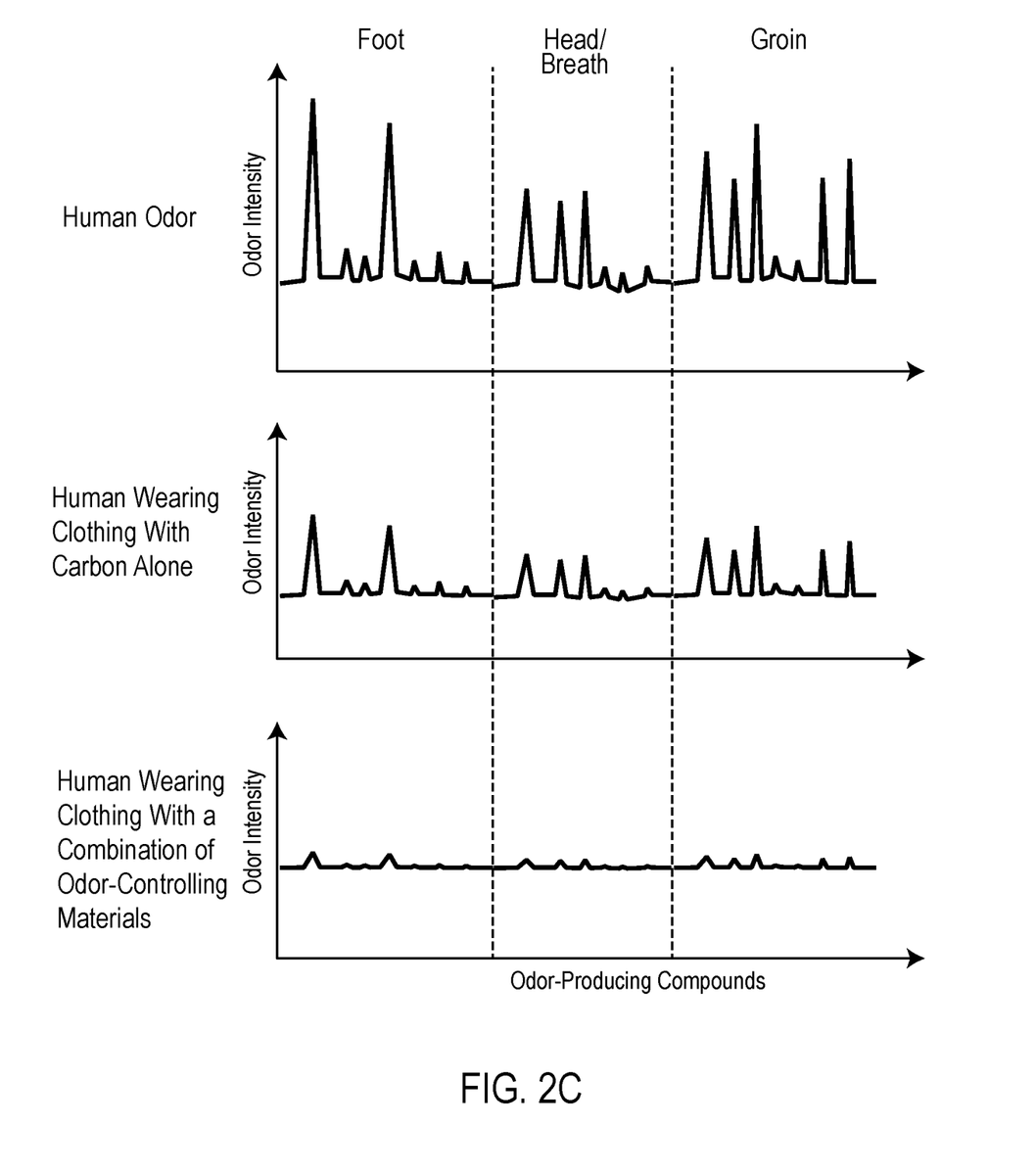
FIG. 2c shows hypothetical odor spectrums for various human body areas, the odor spectrums for a human wearing clothing including activated carbon alone, and the odor spectrums for a human wearing clothing including activated carbon combined with additional materials, according to an exemplary embodiment.

Referring to FIGS. 1-2, a material, such as material associated with clothing, experiences a wide spectrum of human odors (i.e., airborne type volatiles) associated with organic compounds, hydrocarbons, and non-polar gases. Such odors may be impacted by the foods a person eats, bacterial odors, and external scents (e.g., scents from clothes, scents from soaps, etc.). Indeed, human odor may include over 350 identified odors. As shown in FIG. 1, various odors are produced at greater intensities. By way of example, hydrogen sulfide, ammonia, and mercaptan are among the odor peaks labeled in FIG. 1. While FIGS. 1-2 include a hypothetical spectrum of human odor, it should be understood that actual odor profiles may be similar or different from those explicitly shown in FIGS. 1-2. As shown in FIG. 2a, a material including activated carbon alone may produce a hypothetical odor spectrum with most of the peaks flattened or reduced in magnitude. However, various peaks remain pronounced such as those, by way of example, associated with hydrogen sulfide, ammonia, and mercaptan.

Applicant has found that human odors associated with some compounds that are not as effectively adsorbed by activated carbon alone may signal the presence of humans to wild game or other animals. For example, human odors associated with inorganic compounds; polar gases; other elements such as ketone organic compounds, aldehyde organic compounds, or reactive compounds; and other compounds not as effectively adsorbed by activated carbon such as hydrogen sulfide, mercaptan, amines, ammonia, and other compounds may be detectable to target species.

Referring now to FIGS. 2b-2c, a material may include a combination (i.e., amalgam, fusion, assembly, assemblage, blend, mixture, etc.) of odor-controlling materials that synergistically reduce the odor profile of an object. Odors may be controlled directly (e.g., with compounds that interact with odor molecules, etc.) and indirectly (e.g., with compounds that prevent the production of odors, etc.). The combination of odor-controlling materials includes a plurality of materials configured to directly control odor, according to an exemplary embodiment. The combination may include a plurality of carbon-based materials, synthetic materials, both carbon-based and synthetic materials, materials modified from a natural state, or even other materials. The odor-controlling materials may include activated carbon combined (e.g., assembled, blended, mixed, impregnated, treated) with other materials in a manner specifically designed to target and adsorb a spectrum of human odors or scents in a more effective manner than even the best activated carbon alone (e.g., activated carbon formed from coconut shells). Until the invention of the present disclosure, activated carbon alone was thought to be the pinnacle of odor adsorption potential for, by way of example, human odors. The spectrum of FIGS. 1-2 may correspond to all human odors or a subset of human odors particularly detectable by target species such as wild game, tracking dogs, sniffing machine, humans, systems capable of detecting odor, etc. Accordingly, the combination of odor-controlling materials is configured to adsorb or otherwise mask human odors produced from organic as well as inorganic compounds, and compounds that may not be as effectively controlled solely by activated carbon or other singular adsorbents, absorbents, or neutralizers.

The individual ingredients (e.g., components, materials, constituents, etc.) of the combination of odor-controlling materials may be provided in multiple ranges of concentration (i.e., a single material may include various combinations each having different concentrations of the same materials, each having different materials, etc.). According to an exemplary embodiment, not only are various ingredients present in the combination of odor-controlling materials to adsorb specific odors (e.g., different odors associated with different body areas), but the individual ingredients of the combination of odor-controlling materials are provided in concentrations specifically targeted to overcome the magnitude and/or identity of the odors produced by humans (e.g., odors produced at a particular area of the body). However, in other embodiments, some of the ingredients of the combination of odor-controlling materials may be provided in concentrations that exceed or are less than the concentrations necessary to adsorb the associated types of odor that form the spectrum of the human odor profile. The combination of odor-controlling materials may be integrated with (e.g., applied with a liquid, applied in powder form, etc.) a fabric or other components of an article, preferably a camouflage article.

According to an exemplary embodiment, the ingredients are provided uniformly throughout the camouflage article. For example, a particular combination of odor-controlling materials may be provided in a layer of fabric that is used throughout the article. Such a particular combination of odor-controlling materials may alternatively be applied non-uniformly throughout the camouflage article. By way of example, a greater quantity of the combination of odor-controlling materials may be applied to areas configured to be positioned alongside an area of the body that produces a greater odor profile (e.g., the hands, underarms, groin area, etc.).

In other embodiments, different combinations of odor-controlling materials are used in different locations on articles or in different articles of a set of articles (e.g., a set of camouflage clothes). For example, materials configured to adsorb odors commonly emanating from feet are provided in socks, while materials configured to adsorb odors associated with human sweat are provided in the sock as well as a shirt, jacket, pants, hat, gloves, and face mask. In some embodiments, the concentration of the various combinations of odor-controlling materials is increased in underarm areas of shirts and groin areas of pants. In other embodiments, the concentration of certain materials is increased in the area of a mask worn over or near a mouth.

According to an exemplary embodiment, the combination of odor-controlling materials includes activated carbon and at least one of a modified carbon and another material combined with the activated carbon. Pure or untreated activated carbon, such as activated carbon formed from coconut shells or bamboo, may make up the bulk of the combination of odor-controlling materials, and the additional material may be combined with some or all the activated carbon or combined with other carbon and combined with the activated carbon. According to an exemplary embodiment, the additional material is configured to adsorb human odor associated with compounds that may not be entirely adsorbed by activated carbon alone.

In one embodiment, the pure or untreated activated carbon includes carbon formed from at least one of coconut shells and bamboo. Activated carbon formed from coconut shells has a high surface area-to-weight ratio, a high concentration of micro pores of varying sizes to mechanically entrap odors, and is highly adsorptive of volatile organic compounds. In one embodiment, activated carbon formed from coconut shells is laminated between fabric layers of an article of clothing (e.g., introduced onto an inner surface of a fabric layer). Activated carbon formed from bamboo has a lower surface area, more uniform pores, and a fibrous composition, which advantageously wicks moisture when implemented into an article of clothing. Activated carbon formed from bamboo may be slightly less adsorptive than activated carbon formed from coconut shells but may have a higher tensile strength. In one embodiment, activated carbon formed from bamboo is blended with or woven into the fibers of an article of clothing. The combination of odor-controlling materials may include carbon formed from coconut shells, carbon formed from bamboo, or carbon formed from coconut shells and carbon formed from bamboo.

According to an exemplary embodiment, hydrogen sulfide is one example of an inorganic compound producing human odor that may be adsorbed more effectively by a combination of treated activated carbon and activated carbon than by activated carbon alone. As such, the treated activated carbon is combined with the activated carbon to form a combination that is particularly configured to adsorb hydrogen sulfide. Examples of commercially-available carbon treated to adsorb hydrogen sulfide include grade VA3 and VA4 impregnated activated carbon produced by Jacobi Carbons, Inc. or SPARTAN Series enhanced activated carbon manufactured by Carbon Resources. In other embodiments, commercially-available treated activated carbon produced or sold by Eurocarb, Calgon Carbon, Cameron Carbons, Carbonsources.com, or other manufacturers or distributers may be used.

In some embodiments, the activated carbon that is treated to adsorb human odor associated with hydrogen sulfide forms at least 0.1 percent of the total combination of odor-controlling materials, but less than ninety five percent. In preferred embodiments, the activated carbon that is treated to adsorb human odor associated with hydrogen sulfide forms at least five percent, but less than ninety five percent of the total combination of odor-controlling materials for the areas of the body producing sulfur compounds. By way of example, the activated carbon that is treated to adsorb human odor associated with hydrogen sulfide forms at least five percent, but less than ninety five percent of the total combination of odor-controlling materials, for the mouth area and at least five percent, but less than eighty percent of the total combination of odor-controlling materials, for the foot areas.

According to an exemplary embodiment, the combination of odor-controlling materials further comprises a second material combined with the activated carbon. The second material is configured to adsorb human odor associated with at least one of mercaptan and another element not well adsorbed by activated carbon alone or the other odor-controlling materials, according to an exemplary embodiment. In some embodiments, the second material is combined with activated carbon to form a treated activated carbon that is particularly configured to adsorb mercaptan. Such materials include commercially-available grade VA4 impregnated activated carbon produced by Jacobi Carbons, Inc. In other embodiments, impregnated carbon produced or sold by Eurocarb, Calgon Carbon, Cameron Carbons, Carbonsources.com, or other sources may be used.

In some embodiments, the activated carbon that is treated to adsorb human odor associated with mercaptan forms at least 0.1 percent of the total combination of odor-controlling materials, but less than ninety five percent. In a preferred embodiment, the activated carbon that is combined to adsorb human odor associated with mercaptan forms at least five percent, but less than eighty percent of the total combination of odor-controlling materials.

According to an exemplary embodiment, the combination of odor-controlling materials further comprises a third material combined with the activated carbon. The third material is configured to adsorb human odor associated with amines. In some embodiments, the third material is combined with activated carbon to form a treated activated carbon that is particularly configured to adsorb amines, such as commercially-available grade VB1 impregnated activated carbon produced by Jacobi Carbons, Inc. In other embodiments, treated activated carbon produced or sold by Eurocarb, Calgon Carbon, Cameron Carbons, Carbonsources.com, or other sources may be used.

According to an exemplary embodiment, the combination of odor-controlling materials includes a fourth material, which is configured to adsorb human odor associated with ammonia. In some embodiments, the fourth material is ammonia stone or a zeolite. In some such embodiments, a synthetic or natural zeolite may be used, such as at least one of amicite, analcime, barrerite, bellbergite, bikitaite, boggsite, brewsterite, chabazite, clinoptilolite, cowlesite, dachiardite, edingtonite, epistilbite, erionite, faujasite, ferrierite, garronite, gismondine, gmelinite, gobbinsite, gonnardite, goosecreekite, harmotome, herschelite, heulandite, laumontite, levyne, maricopaite, mazzite, merlinoite, mesolite, montesommaite, mordenite, natrolite, offretite, paranatrolite, paulingite, pentasil, perlialite, phillipsite, pollucite, scolecite, sodium dachiardite, stellerite, stilbite, tetranatrolite, thomsonite, tschernichite, wairakite, wellsite, willhendersonite, and yugawaralite. In some embodiments, the zeolite may be dealuminized and hydrophobic such that the zeolite has an affinity for non-polar substances, such as volatile organic compounds.

In some embodiments, the ammonia stone forms less than fifteen percent of the total combination of odor-controlling materials. In one embodiment, the ammonia stone forms at least two percent of the total combination of odor-controlling materials, but less than five percent. In another embodiment, the ammonia stone forms less than two percent of the total combination of odor-controlling materials.

Different materials may have pore sizes that are larger or smaller than those of activated carbon. These larger or smaller pore sizes allow different materials to adsorb larger or smaller odor particles than activated carbon alone. By way of example, zeolite may have a pore diameter much smaller than that of activated carbon. By creating a combination formed from activated carbon, treated carbon, and another component, such as zeolite having a smaller pore diameter, a wider range of odor molecules and compounds may be adsorbed. Still other combinations formed from multiple odor-controlling materials having a wider range of pore sizes and affinities and may adsorb a wider range of odors or may synergistically adsorb odors more completely (e.g., allow for an improved range and potential odor adsorption performance) relative to activated carbon alone. In other embodiments, at least one odor-controlling material of the combination of odor-controlling materials otherwise reduces the likelihood, prevalence, or intensity of an odor.

According to another exemplary embodiment, the combination of odor-controlling materials includes silica gel which is most commonly used as a desiccant as a result of its high capacity for water adsorption. However, silica gel has a pore size distribution which is different from that of activated carbon. Therefore, by creating a combination of activated carbon and another component such as silica gel, the relative range and potential odor adsorption performance of the odor-controlling material can be expanded and improved through the use of multiple odor-controlling materials having varying pore sizes and multiple affinities.

According to still another exemplary embodiment, the combination of odor-controlling materials further includes an odor neutralizer. The odor neutralizer may react with certain odorants to reduce the odor profile of a subject. In one embodiment, the odor neutralizer is an acid neutralizer (e.g., a base) tailored to reduce the odor profile of a mostly-acidic subject (e.g., a human) that produces mostly-acidic odorants. The odor neutralizer includes sodium bicarbonate, sodium hydroxide, calcium carbonate, calcium oxide, calcium hydroxide, magnesium hydroxide, or still another basic material (i.e., a material having a pH of greater than seven), according to an exemplary embodiment. By way of example, the odor neutralizer may neutralize ammonia odors into an odor-neutral ammonium nitrite or ammonium sulfate. In another embodiment, the odor neutralizer is acidic and is configured to neutralize basic odorants. In still other embodiments, the odor neutralizer includes both basic and acidic materials and is configured to neutralize both acidic and basic odorants.

According to yet another exemplary embodiment, the combination of odor-controlling materials further includes an ion exchange material (e.g., an ion exchange resin). The ion exchange material may neutralize the charge of odorants to reduce the odor profile of a subject. By way of example, the ion exchange material may be used to at least one of purify charged compounds and remove ionic molecules from a solution (e.g., air, water, etc.). The ion exchange material may be produced or sold by Bio-Rad, Siemens, Dow, or Lenntech, among other companies. The ion exchange material neutralizes the charge of odorants having a wide range of pH values, according to an exemplary embodiment. The ion exchange material may be any combination of strongly-basic, strongly-acidic, weakly-acidic, or weakly-basic. In one embodiment, the ion exchange material is a catatonic (i.e., positively charged) polymer tailored to reduce the odor profile of a subject (e.g., a human) that produces mostly-anionic (i.e., negatively charged) odorants. The odor neutralizer includes quaternary polyamines, according to an exemplary embodiment. In another embodiment, the ion exchange material is negatively charged and neutralizes positively charged odorants. In still other embodiments, the ion exchange material includes both negatively and positively charged materials to neutralize both positively and negatively charged odorants.

Different combinations of odor-controlling materials are provided in different locations on articles of clothing or in different articles of clothing, according to an exemplary embodiment. As shown below in Table 1, various odor-controlling materials are provided in weight percentages that are tailored for a particular location on an article of clothing or for different articles of clothing. According to various alternative embodiments, the combination does not include at least one of the odor-controlling materials identified for a particular area of the body or the combination includes the odor-controlling materials at different weight percentages. Additional odor-controlling materials may be added or substituted for those listed, according to still other alternative embodiments. In one embodiment, a base layer (e.g., a shirt, pants, etc.) includes the combination identified as "Full Body Next to Skin," and a layering shirt or pants (i.e., a mid layer, an external shell layer, etc.) may include the combination identified as "Full Body Away from Skin." A face mask may include the combination identified as "Mouth" in an area configured to be worn around a user's mouth and the combination identified as "Hair" in an area configured to be worn around the user's scalp. Socks may include the combination identified as "Feet." Shirts, pants, and/or coveralls (e.g., base layers, mid layers, external shells, etc.) may include the combination identified as "Axial Area" in areas configured to be worn around a user's groin or armpits.

TABLE 1

Odor-Controlling Materials

| | | Carbon | Treated Carbon | Zeolite | Neutralizers | Other |
|---|---|---|---|---|---|---|
| Areas of the Body | Full Body Next to Skin | 59-99.5% (e.g., 91%) | 0.25-20% (e.g., 5%) | ≤15% (e.g., 1%) | 0.25-6% (e.g., 3%) | |
| | Full Body Away from Skin | 59-99.5% (e.g., 92.5%) | 0.25-20% (e.g., 2%) | ≤15% (e.g., 4%) | 0.25-6% (e.g., 1.5%) | |
| | Mouth | ≤90.75% (e.g., 37%) | 5-95% (e.g., 50%) | 2-5% (e.g., 5%) | 2-5% (e.g., 3%) | 0.25-5% (e.g., 5%) |
| | Hair | 87-99.7% (e.g., 91%) | 0.1-7% (e.g., 7%) | 0.1-1% (e.g., 1%) | 0.1-3% (e.g., 1%) | ≤2% |
| | Axial Area | 72-99% (e.g., 88.5%) | 1-20% (e.g., 9%) | ≤2% (e.g., 1.5%) | ≤6% (e.g., 1%) | |
| | Feet | ≤94% (e.g., 42%) | 5-80% (e.g., 50%) | ≤2% (e.g., 2%) | 1-20% (e.g., 6%) | ≤3% |

A commercial embodiment of the present invention was tested and compared with products employing various odor-controlling technologies. Specifically, Applicant compared a fabric layer including an antimicrobial material, a fabric layer including zeolites, a fabric including a bamboo carbon yarn, and various other products to a commercial embodiment of the present invention. Applicant's testing showed that the commercial embodiment of the present invention offers significantly greater odor permeability performance and odor adsorption capacity relative to the tested products.

In some embodiments, the combination of odor-controlling materials may include only physical adsorbents (e.g., activated carbon, zeolite, activated carbon treated to adsorb hydrogen sulfide, synthetic materials, etc.). According to an exemplary embodiment, the physical adsorbents have structural features (e.g., arms, voids, cavities, surfaces, etc.) that interact with an odorant to physically capture the odor molecule and thereby reduce the odor profile of an object. By way of example, an article of clothing may include physical adsorbents having cavities that entrap human odors. By way of another example, a surface may include physical adsorbents having cavities that entrap odorants that engage the surface. While physical adsorbents may have a reduced effectiveness after extensive use (e.g., because odorants occupy a portion of the cavities), odorants may be removed from the physical adsorbents by applying heat (e.g., by placing an article of clothing containing the physical adsorbents in a household dryer), which is a process known as reactivation. Thereafter, the physical adsorbent may have an improved effectiveness.

In other embodiments, the combination of odor-controlling materials may include physical adsorbents and chemical adsorbents (e.g., carbon tetrachloride, potassium permanganate, a thiol, a catalytic oxidizer, another oxidizer, etc.). The chemical and physical adsorbents may synergistically improve the adsorption characteristics of the combination of odor-controlling materials. Various molecules such as acetaldehyde, acetylene, arsenic, carbon dioxide, ethylene, formaldehyde, hydrazine, hydrogen cyanide, nitric acids, nitrogen dioxide, sulfur dioxide, and other molecules may be more effectively adsorbed with chemical adsorbents than with physical adsorbents. Chemical adsorbents may also be configured to dissolve non-polar compounds, fats, oils, and iodine. In contemplated embodiments, the chemical adsorbent may include a material to adsorb at least one of trimethylamine associated with body odor, dimethyl sulfide associated with breath odor, isobutyraldehyde associated with fatty acids, ethanol associated with breath and body odor, isovaleric acid associated with sweat or odors from bacteria, and limonene associated with pubic axillary odor.

According to an exemplary embodiment, the chemical adsorbents include molecules that react with odorants to reduce the odor profile of an object. By way of example, an article of clothing may include chemical adsorbents that react with human odors. By way of another example, a surface may include chemical adsorbents that react with odorants that engage the surface. While odorants may be removed from physical adsorbents, chemical adsorbents may be consumed during the reaction process such that odorants may not be removable from the chemical adsorbents. Further, chemical adsorbents may have a reduced effectiveness after use. Therefore, a product may include a specified quantity (e.g., an amount that is not likely to be consumed during the anticipated life of the product, another amount, etc.) of chemical adsorbents.

In some embodiments, the combination of odor-controlling materials includes a synthetic polymer (e.g., polymeric adsorbent), such as commercially available resins made with copolymers of styrene, divinyl benzene and acrylic acid ester, and divinyl benzene that may be integrated into a layer of articles to adsorb human odors associated with ketone, aldeyde, and reactive compounds in a more-efficient manner than carbon alone. Polymers generally have greater ranges of pore sizes than zeolite. In some embodiments, Conpol 20LO produced by DuPont is included in the combination. In contemplated embodiments, nano-structures such as nano-tubes formed to contain the combination of odor-controlling materials, may be used to control odors (e.g., on an atomic level). In other such embodiments, nano-coatings of titanium dioxide on articles may be used to prevent airborne contaminants (e.g., molds, bacteria) from adhering to surfaces.

While some particular materials are described herein for adsorbing particular human odors, other elements or materials may be combined with carbon or other materials to form a combination of odor-controlling materials that adsorbs a different specific spectrum of odor. Additionally, the combination of odor-controlling materials may include one or more (or all) of the combination materials disclosed herein, where each one provides synergistic enhancements to the combination of odor-controlling materials relative to the others.

Some additional disclosure relating to olfactory concealment is provided in U.S. Pat. No. 6,000,057, which is incorporated by reference herein in its entirety, where materials, articles, and methods disclosed therein may be incorporated or combined in full or in part with materials, articles, and methods disclosed herein. The materials disclosed in U.S. Pat. No. 6,000,057 may be used together in unique combinations, concentrations, and locations in articles, as disclosed herein.

Figure 3:
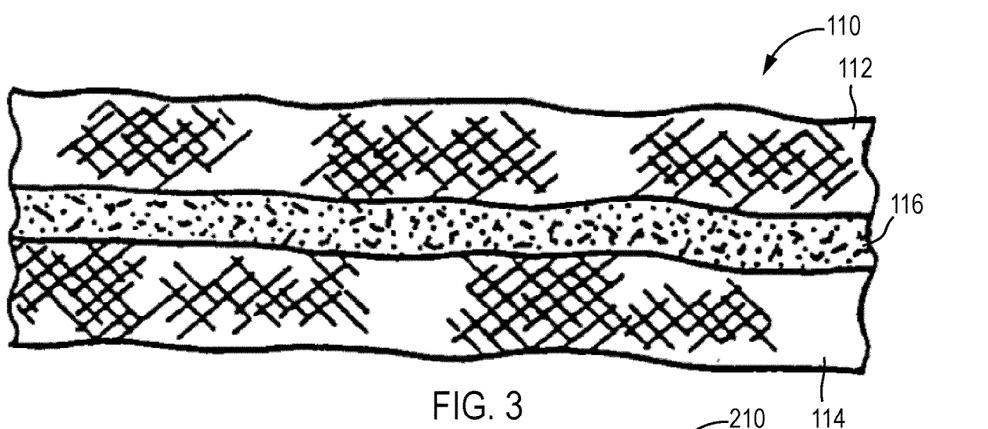
FIG. 3 is a sectional view of fabric including an interior layer of odor adsorbing materials, according to an exemplary embodiment.

Referring next to FIG. 3, an article 110 includes a base layer (e.g., cloth, fabric, plastic, or other material) arranged in a first layer 112 of fabric and a second layer 114 of fabric, according to an exemplary embodiment. The cloth may be formed from organic or synthetic materials (e.g., cotton, Gore Tex®, rayon, etc.). In some embodiments, the cloth is air permeable or breathable. In some embodiments, the cloth is insulated, waterproof, water resistant, fireproof, windproof or wind resistant. Between the layers 112, 114, the article 110 includes a combination of odor-controlling materials 116 particularly configured to adsorb a spectrum of human odor that is greater than the spectrum adsorbed solely by any singular compound or element. In other embodiments, the combination of odor-controlling materials 116 is coupled to (e.g., impregnated onto, integrated into, integrated between layers of, formulated as part of, etc.) at least one of a mesh, a nonwoven material, a fluidized bed, an aerosol or liquid material (e.g., a material that leaves an odor-controlling film). As such, wild game animals that may detect human odors not adsorbed by activated carbon may not detect the odors of a human wearing camouflage containing the combination of odor-controlling materials 116.

According to an exemplary embodiment, to achieve clothing that adsorbs human odor to avoid detection, especially by wild game, the combination of odor-controlling materials 116 in the clothing includes a combination to enhance the adsorption capacity of the clothing. The combination of odor-controlling materials 116 may also provide the capability of effectively adsorbing a broader spectrum of odors than just activated carbon or a single element or compound. Furthermore, the combination of odor-controlling materials 116 may be formulated to specifically target human effluent odors of all kinds and to optimize for maximum adsorption of human-specific odors, reducing the human odor profile to few odors of any kind, including odors that are not trapped well or at all by activated carbon or any single element or compound.

Figure 4:
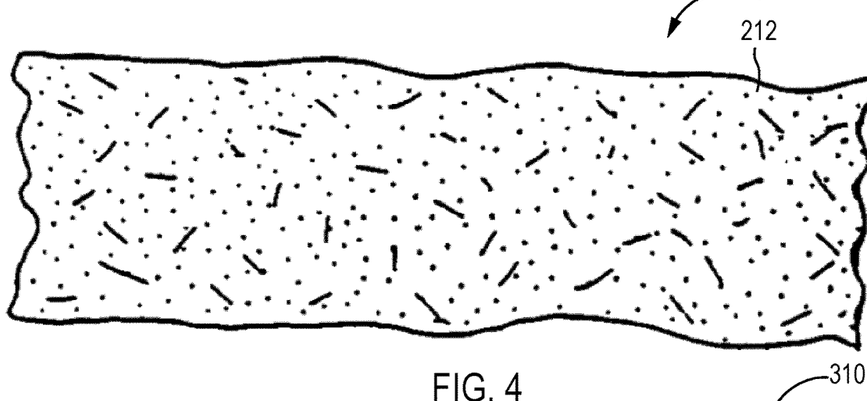
FIG. 4 is a sectional view of fabric including odor adsorbing materials, according to an exemplary embodiment.
Figure 5:
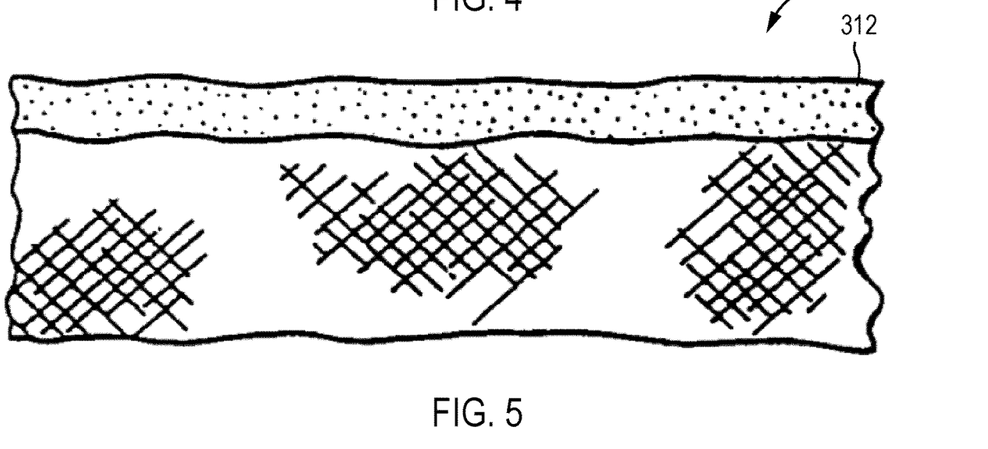
FIG. 5 is a sectional view of fabric including an exterior layer of odor adsorbing materials, according to an exemplary embodiment.

Referring to FIGS. 3-5, the combination of odor-controlling materials 212 may be combined with a composite cloth 210 or fabric, as opposed to being positioned in a discrete layer between layers of the fabric, as shown in FIG. 3. In some such embodiments, the combination of odor-controlling materials 212 may be coated or otherwise integrated with individual threads or filaments of the composite cloth 210. Also, the combination of odor-controlling materials 312 may be layered on an exterior of the cloth 310 (e.g., outer surface, an inner surface, or both), as shown in FIG. 5. In some such embodiments, the combination of odor-controlling materials 312 may be applied to the cloth 310 during manufacturing of the cloth 310, applied afterward by a hunter in the field, or a combination of these methods In some embodiments, the combination of odor-controlling materials may be applied in a single layer in or on cloth of an article. In other embodiments, the combination of odor-controlling materials may be provided on, in, or between multiple layers of cloth or on the surfaces thereof. The combination of odor-controlling materials may be mechanically attached, adhesively attached, or otherwise coupled to the cloth (e.g., on the surface thereof). Alternatively, the combination of odor-controlling materials may be integrated in a foam, a powder, cream, or a spray medium for field application. Further discussion of integrating an odor-concealing material in a fabric is provided in U.S. Pat. No. 5,383,236, which is incorporated by reference herein in its entirety, where materials, articles, and methods disclosed therein may be incorporated or combined in full or in part with materials, articles, and methods disclosed herein.

Figure 6:
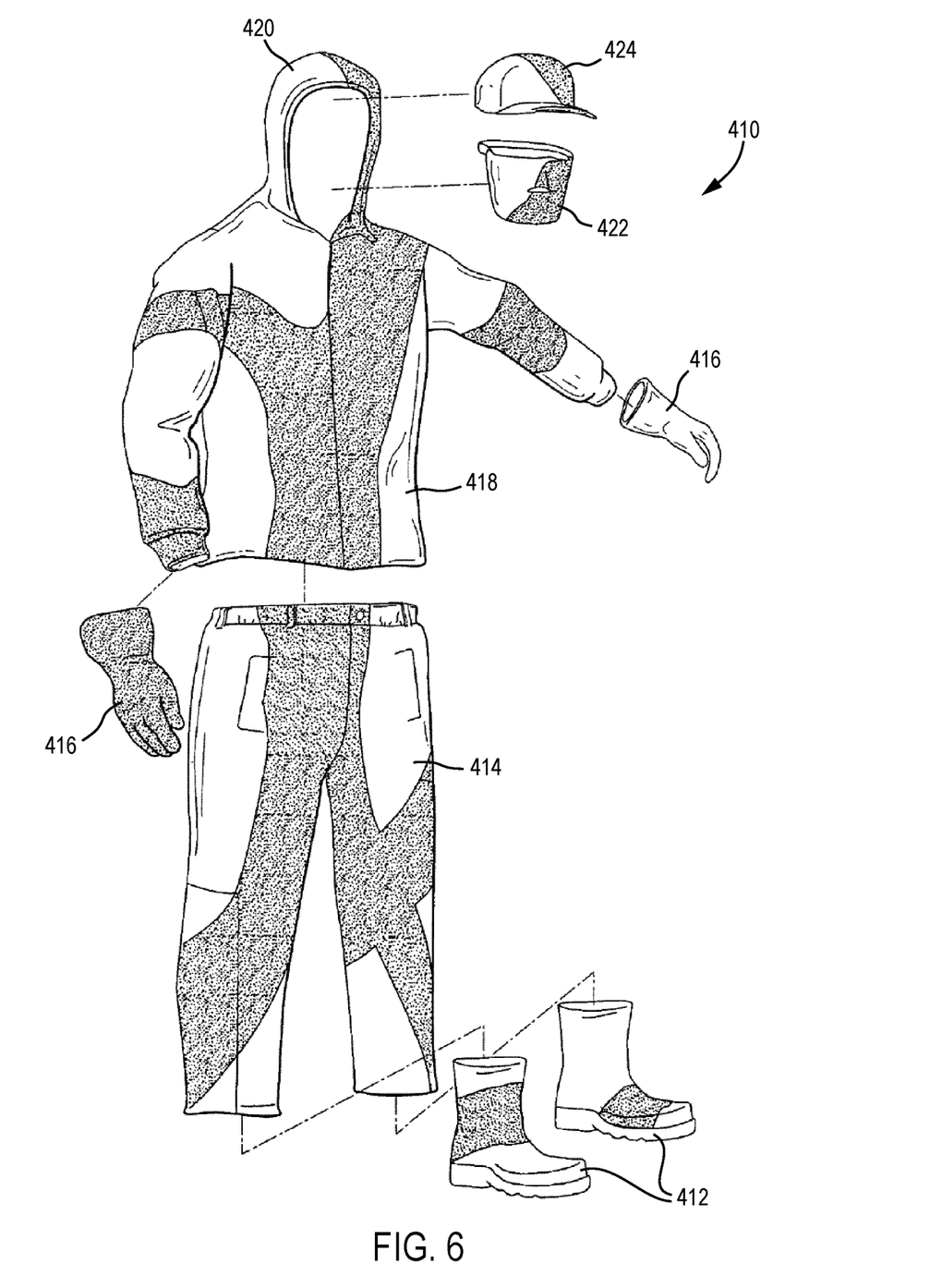
FIG. 6 is a camouflage outfit at least partially formed from fabric as shown in FIGS. 3-5, according to an exemplary embodiment.
Figure 7:
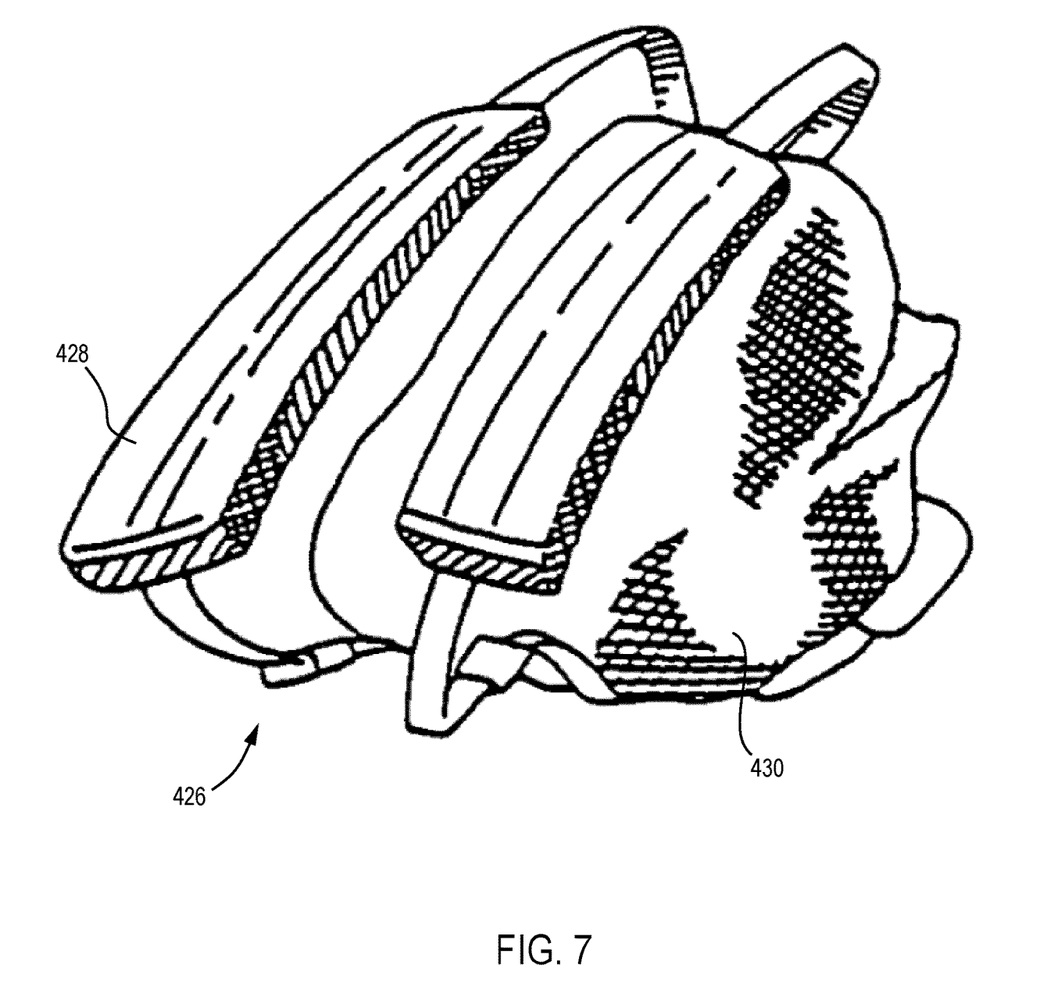
FIG. 7 is a sack at least partially formed from fabric as shown in FIGS. 3-5, according to an exemplary embodiment.

Referring now to FIGS. 6-7, a camouflage outfit 410 is at least partially formed from cloth 110, 210, 310 as described herein, where the cloth 110, 210, 310 includes one or more of the combinations of odor-controlling materials 116, 212, 312 configured to adsorb human odors. The outfit 410 includes various articles, such as boots 412, pants 414, gloves 416, a shirt 418, a hood 420, a mask 422, and a hat 424. Some or all of the articles of the outfit 410 may include the combination of odor-controlling materials 116, 212, 312. In some embodiments, the outfit 410 may further include a sack 426, bag, or other articles, as shown in FIG. 7, where a portion of the sack 426, such as the shoulder straps 428 or bag portion 430 of the sack 426, includes the combination of odor-controlling materials 116, 212, 312. In other embodiments, a box is formed by a plurality of sidewalls and includes a combination of odor-controlling materials to control the odors of products (e.g., articles of clothing) stored therein.

According to an exemplary embodiment, a combination of odor-controlling materials may be configured for specific uses. In some embodiments, the combination of odor-controlling materials is used in various articles and specifically adsorbs or otherwise masks a spectrum of odors produced by different body areas or parts by humans that are detectable by animals. In other embodiments, the combination of odor-controlling materials is used in cold-weather gear for in-field biologists observing arctic animals, such as polar bears. In still other embodiments, the combination of odor-controlling materials may be used in military flight suits for evasion from tracking-dogs by downed pilots. In some embodiments, the combination of odor-controlling materials is used to adsorb human odors detectable by other humans, such as odors that may be offensive to humans. Still other embodiments are contemplated and fall within the scope of this disclosure.

According to an alternative embodiment, the combination of odor-controlling materials may adsorb odors produced by other sources. In some embodiments, the combination of odor-controlling materials may synergistically reduce the odor profile of the source. The combination of odor-controlling materials may be applied to a surface (e.g., a fabric, an article, a polymeric sheet, a synthetic surface, a metallic surface, etc.) and configured to adsorb various odorants. By way of example, the combination of odor-controlling materials may be integrated into an article and configured to adsorb odors associated with an animal (e.g., a dog, a farm animal, etc.). By way of another example, the combination of odor-controlling materials may be integrated into a polymeric sheet and configured to adsorb odors associated with a chemical process, odors produced as fumes, or odors from still other sources. In some embodiments, the combination of odor-controlling materials may be tailored to reduce the odor profile of a specific source. By way of example, various physical or chemical adsorbents, such as those discussed herein, may be selected to adsorb odors that correspond with the odor spectrum of a target source. In some embodiments, the combination of odor-controlling materials may be differentially applied at different portions of the surface or different combinations of odor-controlling materials may be applied at different portions of the surface to target particular areas of a source differently.

According to an exemplary embodiment, the combination of odor-controlling materials may be distributed evenly over cloth of some or all of the articles. In other embodiments, individual materials of the combination of materials may further be concentrated or distributed in particular articles or locations on articles associated with areas of the human body that produce particular odors. By way of example, mercaptan-adsorbing material or other adsorbents may be integrated within footwear to reduce the impact of isovaleric acids or pathogens. In other embodiments, sulfide-adsorbing material or other adsorbents may be integrated within a mask to reduce the impact of sulfides. As a further example, $C_2$-$C_5$ compounds, aliphatic acids, trimethylamine, apocrine or sebaceous gland compounds, i-pyrrolines may be associated with the inner thigh and groin area whereas androgen compounds and acrid compounds may be associated with the underarm area. Still other endogenous and exogenous odors may be associated with the arms, legs, or other areas of the body. Particular materials may be included in the combination to target these or other odors.

Applicant notes that all percentages of ingredient materials disclosed herein are percentage by weight of a larger composition of materials. Furthermore, as will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, include the number recited and refer to ranges which can be subsequently broken down into subranges as discussed above. Finally, as will be understood by one skilled in the art, a range includes each individual member.

The construction and arrangements of the systems and methods for controlling odors, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. In contemplated embodiments, a suit or jacket for a hunting dog may similarly include a combination of odor-adsorbing materials, more than activated carbon such as one or more of the materials disclosed herein, to improve adsorption of odors associated with dogs to target species. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A scent reducing article of clothing including material arranged to form a jacket, the article comprising:
    a cloth comprising one or more pieces of the material arranged to form the jacket, the jacket having a torso portion, a pair of underarm portions adjacent the torso portion, and a pair of arms, one of each of the arms being adjacent one of each of the underarm portions, at least one of the torso portion and the pair of arms defining a first area and the pair of underarm portions defining a second area;
    a first assembly including one or more scent control materials provided within the first area defined by the cloth; and
    a second assembly including one or more scent control materials provided within the second area defined by the cloth, the second assembly having a different composition than the first assembly,
    wherein the first assembly and the second assembly together include activated carbon and at least one of carbon treated to adsorb hydrogen sulfide, zeolite, ammonia stone, and carbon treated to adsorb mercaptan.

2. The article of claim 1, wherein the first assembly and the second assembly both include a common scent control material, the second assembly having a greater concentration of the common scent control material than the first assembly.

3. The article of claim 1, wherein the cloth comprises a camouflage pattern.

4. The article of claim 1, wherein the cloth is insulated.

5. The article of claim 1, wherein the cloth is waterproof.

6. The article of claim 1, wherein the cloth is windproof.

7. A scent reducing article of clothing including material arranged to form a shirt, the article comprising:
    a cloth comprising one or more pieces of the material arranged to form the shirt, the shirt having a torso portion, a pair of underarm portions adjacent the torso portion, and a pair of arms, one of each of the arms being adjacent one of each of the underarm portions, at least one of the torso portion and the pair of arms defining a first area and the pair of underarm portions defining a second area;
    a first assembly including one or more scent control materials provided within the first area defined by the cloth; and
    a second assembly including one or more scent control materials provided within the second area defined by the cloth, the second assembly having a different composition than the first assembly,
    wherein the first assembly and the second assembly together include activated carbon and at least one of carbon treated to adsorb hydrogen sulfide, zeolite, ammonia stone, and carbon treated to adsorb mercaptan.

8. The article of claim 7, wherein the first assembly and the second assembly both include a common scent control material, the second assembly having a greater concentration of the common scent control material than the first assembly.

9. The article of claim 7, wherein the cloth comprises a camouflage pattern.

10. The article of claim 7, wherein the cloth is insulated.

11. The article of claim 7, wherein the cloth is waterproof.

12. The article of claim 7, wherein the cloth is windproof.

13. A scent reducing article of clothing including material arranged to form pants, the article comprising:
- a cloth comprising one or more pieces of the material arranged to form the pants, the pants having a pair of leg sections adjacent a groin region, the pair of leg sections defining a first area and the groin region defining a second area;
- a first assembly including one or more scent control materials provided within the first area defined by the cloth; and
- a second assembly including one or more scent control materials provided within the second area defined by the cloth, the second assembly having a different composition than the first assembly, wherein the first assembly and the second assembly together include activated carbon and at least one of carbon treated to adsorb hydrogen sulfide, zeolite, ammonia stone, and carbon treated to adsorb mercaptan.

14. The article of claim 13, wherein the first assembly and the second assembly both include a common scent control material, the second assembly having a greater concentration of the common scent control material than the first assembly.

15. The article of claim 14, wherein the cloth comprises a camouflage pattern.

16. The article of claim 15, wherein the cloth is waterproof.

17. The article of claim 13, wherein the cloth comprises a camouflage pattern.

18. The article of claim 13, wherein the cloth is insulated.

19. The article of claim 13, wherein the cloth is waterproof.

20. The article of claim 13, wherein the cloth is windproof.

* * * * *